United States Patent [19]

Lee et al.

[11] Patent Number: 4,473,706
[45] Date of Patent: Sep. 25, 1984

[54] PREPARATION OF CYCLIC-KETO-ACIDS

[75] Inventors: John Y. Lee; Thomas J. Walter, both of Baton Rouge, La.

[73] Assignee: Ethyl Corporation, Richmond, Va.

[21] Appl. No.: 405,816

[22] Filed: Aug. 6, 1982

[51] Int. Cl.$^3$ ............................................. C07C 61/04
[52] U.S. Cl. .................................... 562/506; 562/497; 562/520
[58] Field of Search ................ 562/497, 506, 496, 520; 260/502 R

[56] References Cited

U.S. PATENT DOCUMENTS

| | | | |
|---|---|---|---|
| 2,874,186 | 2/1959 | Friedman | 562/497 |
| 3,665,034 | 5/1972 | Komotsu et al. | 562/497 |
| 3,816,488 | 6/1974 | Cradock et al. | 562/497 |
| 4,152,352 | 5/1979 | Perron | 562/497 |

FOREIGN PATENT DOCUMENTS

| | | | |
|---|---|---|---|
| 4808701 | 6/1971 | Japan | 568/497 |
| 2026478 | 2/1980 | United Kingdom | 568/497 |

OTHER PUBLICATIONS

Robb "The Chemistry of Carbon Compounds", vol. 1, (1952 Ed.) pp. 227–229.
Francalanci et al., "J. Electroanalytical Chemistry" (1982), pp. 59–70, Elsevier Sequoia S. A., Lausanne—Printed in The Netherlands.

Primary Examiner—Werren B. Lone
Attorney, Agent, or Firm—Donald L. Johnson; John F. Sieberth; John F. Hunt

[57] ABSTRACT

Cyclic-keto-acids of the general formula:

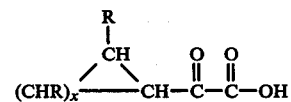

wherein R is hydrogen or a monovalent alkyl radical which can be either straight chain or branched having from 1 to about 20 carbon atoms and X=1, 3, or 4, are prepared by reacting a functionalized 1-bromoalkane of the formula:

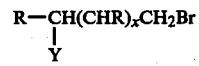

wherein R and X are as defined above and Y is a leaving group, preferably the halogens, in a liquid solvent medium with carbon monoxide at elevated temperature and pressure in the presence of a catalytic amount of a metal carbonyl compound and an alkali or an alkaline earth metal inorganic base.

18 Claims, No Drawings

PREPARATION OF CYCLIC-KETO-ACIDS

TECHNICAL FIELD

The present invention relates to a process for the carbonylation of a functionalized 1-bromoalkane to form a cyclic-keto-carboxylic acid as the predominant product.

The practical value of such acids and their esters is that they can be used in the synthesis of pharmaceuticals, such as steroids, and for preparing herbicides.

BACKGROUND

The preparation of α-keto-carboxylic acids and their derivatives has been the subject of a large number of investigations. According to Rodd, *The Chemistry of Carbon Compounds* (1952 edition), Vol. 1, pages 227–229, the following methods of preparation are available:

- gentle oxidation of α-hydroxyacids containing a secondary hydroxyl group, or by the enzymatic deamination of α-amino-acids;
- hydrolysis of an acyl cyanide;
- hydrolysis of α-oximino-esters;
- from glycidic acid esters on treatment with benzene saturated with boron trifluoride;
- from α,β-dibromocarboxylic acids by forming a piperidine addition compound followed by hydrolysis;
- from α-keto-acetals by ultraviolet irradiation in the presence of N—bromosuccinimide;
- from α-bromomethylketones by boiling with selenium dioxide in absolute methanol or ethanol;
- from carboxylic acid esters by oxidation with selenium dioxide;
- permanganate oxidation of vinyl ketones;
- from carboxylic acid esters by condensation with oxalic ester followed by decarboxylation;
- from aldehydes via 5-alkylidene-2-thio-oxazolid-4-ones or by reaction with methyl methoxyacetate; hydrolysis of azlactones or acetamido-acrylic acids; hydrolysis of the reaction product of Grignard reagents on diethyl-oxamic ester;
- oxidation of α-hydroxyacid esters containing two β-hydrogen atoms by N—boromosuccinimide in carbon tetrachloride to β-bromo-α-keto-acid esters; and by the action of alkali on the dimethanesulphonates and ditoluene-p-sulphonates of α,β-dihydroxy-carboxylic acids.

Methods for preparing arylpyruvic acids also are known. For example, U.S. Pat. No. 4,152,352 discloses the preparation of an arylpyruvic acid by reacting an arylmethyl halide in a liquid solvent medium with carbon monoxide at pressures 5 to 200 bars in the presence of a catalytic amount of a metal carbonyl compound and an alkaline earth metal inorganic base. Further, U. K. patent application No. 2,026,478A discloses that alkali metal salts of an arylpyruvic acid can be prepared by reacting an arylmethyl halide, carbon monoxide and an alkali metal base in the presence of a metal carbonyl compound as catalyst and in the presence of an alcohol or cyclic ether as solvent.

In co-pending U.S. application Ser. No. 353,440, entitled "PROCESS FOR PREPARING ARYLALKYPYRUVIC ACIDS," filed Mar. 1, 1982, there is disclosed a method of preparing certain arylalkypyruvic acids by carbonylating a suitable arylalky halide in a liquid solvent medium with carbon monoxide at elevated temperature and pressure in the presence of a metal carbonyl compound and an alkali or an alkaline earth metal inorganic base. Further, in co-pending U.S. Application Serial No. 353,473, entitled "PROCESS FOR PREPARING ALKYL ALPHA-KETO-CARBOXYLIC ACIDS FROM ALKYL HALIDES," filed Mar. 1, 1982, the preparation of alkyl-α-keto-carboxylic acids by reacting a primary alkyl halide in a liquid solvent medium with carbon monoxide in the presence of a catalytic amount of a metal carbonyl and an inorganic base is disclosed. Still further, in co-pending U.S. Application Serial No. U.S. Ser. No. 405,817, entitled "PROCESS FOR PREPARING β-SUBSTITUTED-α-KETO-CARBOXYLIC ACIDS," filed Aug. 6, 1982, there is disclosed the preparation of β-substituted-α-keto-carboxylic acids by reacting a secondary halide with carbon monoxide in the presence of a metal carbonyl catalyst and an inorganic base.

The cobalt-catalyzed carbonylation of secondary benzyl halides to give either monocarbonyl or double carbonyl insertion or coupling of organic halides is reported by E. Francalanci et. al., *Journal of Electroanalytical Chemistry*, 1982, pp. 59–70.

THE INVENTION

It has now been found that cyclic-keto-acids of the general formula:

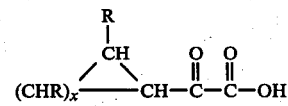

in which R represents hydrogen or a monovalent alkyl radical which can be either straight chain or branched containing from 1 to about 20 carbon atoms, and X=1, 3, or 4 can be prepared by carbonylating a functionalized 1-bromoalkane of the general formula:

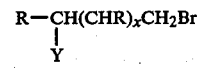

where R and X are as defined above and Y is a leaving group, preferably a halogen, in a liquid solvent medium, with carbon monoxide at a pressure of from about 300 to 3000 psig in the presence of a catalytic amount of a metal carbonyl compound and an alkali or alkaline earth metal inorganic base.

The functionalized 1-bromoalkane reactants suitable for use in the present process are well known in the art as are methods for their preparation and, as defined above, are of the general formula:

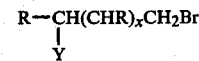

when R is hydrogen or a monovalent alkyl radical which can be either straight chain or branched containing from 1 to about 20 carbon atoms, X=1, 3, or 4 and Y is a suitable leaving group, preferably the halogens viz., iodine, bromine, and most preferably chlorine. Other suitable leaving groups, such as, for example, nitrates, sulfonates and acetates also may be used with the proviso that under the reaction conditions of the instant process, hydrolysis does not become a major competing reaction with the resultant production of unwanted alcohols as the major product. A few exemplary materials of this type include 1-bromo-3-chloro-or 3-bromopropane, butane, pentane, hexane, heptane, octane, nonane, decane, undecane, dodecane, tridecane, tetradecane, pentadecane, hexadecane, heptadecane, octadecane, nonadecane, eicosane, and the like; 1-bromo-5-chloro- or 5-bromopentane, hexane, heptane, octane, nonane, decane, undecane, dodecane, tridecane, tetradecane, pentadecane, hexadecane, heptadecane, octadecane, nonadecane, eicosane, and the like; 1-bromo-6-chloro- or 6-bromohexane, heptane, octane, nonane, decane, undecane, dodecane, tridecane, tetradecane, pentadecane, hexadecane, heptadecane, octadecane, nonadecane, eicosane and the like; the nitrate, sulfonate and acetate esters of 1-bromo-3-hydroxypropane, butane, pentane, hexane, heptane, octane, nonane, decane, undecane, dodecane, tridecane, tetradecane, pentadecane, hexadecane, heptadecane, octadecane, nonadecane, eicosane and the like; the nitrate, sulfonate and acetate esters of 1-bromo-5-hydroxypentane, hexane, heptane, octane, nonane, decane, undecane, dodecane, tridecane, tetradecane, pentadecane, hexadecane, heptadecane, octadecane, nonadecane, eicosane and so forth. A particularly useful reactant is 1-bromo-3-chloropropane from which cyclopropylglyoxylic acid (a precursor for the synthesis of steroids) is produced by the process of the present invention.

The reaction is carried out in the presence of a mixture of water and alcohol as a reaction medium. Preferably, the alcohols employed for the reaction may be straight-chain, branched or cyclic, and preferably contain up to 6 carbon atoms. Methanol, ethanol, propanol, isopropanol, n-butanol, isobutanol, tert-butanol, and tert-amyl alcohol may be mentioned as examples. Cyclic ethers, such as tetrahydrofuran, also may be used. A particularly preferred solvent alcohol is tert-butanol. Mixtures containing about 10% to 90% by weight of water and about 90% to 10% by weight of alcohol generally are used. Preferred mixtures contain about 30% to 80% by weight water and about 70% to 20% by weight alcohol.

The reaction takes place in the presence of a basic substance suitably an alkali or an allkaline earth metal hydroxide employing a metal carbonyl compound. During the reaction, the 1-bromoalkane undergoes reaction with the carbon monoxide and basic substance whereby the salt of the desired cyclic-keto-carboxylic acid is formed from which the cyclic-keto-carboxylic acid is isolated after acidification in a known manner. It is believed that the salt of the keto acid is formed first followed by intramolecular nucleophilic displacement under the alkaline conditions of the reaction medium to form the cyclic keto acid.

Specific examples of suitable basic agents which can be used in the practice of the process include; LiOH, NaOH, KOH, RbOH, $Ca(OH)_2$, $Ba(OH)_2$ and $Mg(OH)_2$. LiOH and $Ca(OH)_2$ are particularly preferred. Yields of cyclic-keto-carboxylic acids of up to approximately 62% can be obtained using $Ca(OH)_2$ as the basic substance and a solvent medium of tert-butanol and water.

The amount of basic agent used can vary within wide limits. In general, the molar ratio of the alkali metal or alkaline earth metal base to 1-bromoalkane reactant is preferably 10:1 to 1:1.

In the process described herein, it is preferred to use metal carbonyl compounds as carbonylation catalysts. These catalysts include particularly metal carbonyls such as iron pentacarbonyl, dicobalt-octacarbonyl and nickel-tetracarbonyl, of their salts such as, for example, the calcium, potassium or sodium salts thereof. Dicobalt-octacarbonyl is very particularly suited. These catalysts can be added to the medium in the solid state or in the form of solutions in the solvent used for the carbonylation reaction. The molar percentage of the metal carbonyl compound to the 1-bromoalkane reactant is preferably from about 0.1 to about 25%.

The concentration of the 1-bromoalkane used in the reaction solvent is not critical and can vary within wide limits. Thus, it can be between about 1 to 30% by weight, based on the weight of the solvent, however, it is possible to go outside of these limits without disadvantage.

The present process is advantageously carried out by bringing the mixture consisting of the 1-bromoalkane reactant, the metal carbonyl catalyst and the alkali or alkaline earth metal base, suspended in the mixture of water and alcohol, into contact, under nitrogen, in a suitable pressure-resistant reactor equipped with a stirrer, with a large excess of carbon monoxide (amount greater than 2 moles of carbon monoxide per mole of the starting 1-bromoalkane reactant) introduced at the desired pressure and temperature, in accordance with techniques suitable for bringing about the reaction between a liquid phase and a gas phase.

The carbonylation reaction is carried out at a temperature in the range of from about 30° C. to about 150° C., preferably from about 50° C. to 100° C., over a period of time of from about 3 to 60 hours, typically 3 to 20 hours.

In general, the reaction takes place at elevated carbon monoxide pressures which may range from about 300 psig to about 3000 psig. Preferably, the reaction takes place at a pressure in the range of about 500 psig to 1000 psig. The carbon monoxide may contain or be mixed with an inert gas, such as nitrogen.

On completion of the reaction, the product mixture is filtered, resulting in the alkali metal or alkaline earth metal salt of the cyclic-keto-carboxylic acid being separated from the liquid reaction components as the main solid component. The filtrate contains the remainder of the alkali or alkaline earth metal salt of the cylic-keto-carboxylic acid, and, where unbranched alcohols are used, also esters in addition to unreacted 1-bromoalkane as well as acid and alcohol products from the starting 1-bromoalkane.

In a further process step, the metal salt of the cylic-keto-carboxylic acid is acidified with a dilute acid, such as hydrochloric acid, so as to displace the cyclic-keto-carboxylic acid from its alkali or alkaline earth metal salt.

If desired, lower alkyl esters of the cyclic-keto-carboxylic acid products of the present invention can be prepared by esterifying the cyclic-keto-carboxylic acid product according to conventional esterification techniques employing lower aliphatic alkanol and acid catalysts such as, for example, $BF_3$, $BF_3.HCl$, or $BF_3.MeOH$, $BF_3.Et_2O$ or diazomethane at suitable reaction conditions.

The following example illustrates the invention.

EXAMPLE 1

Into a 300 ml autoclave were charged 7.87 g (50 mmoles) of 1-chloro-3-bromopropane and 70 ml of t-BuOH. Next, 0.682 g (2 mmoles) of $Co_2(CO)_8$ were added under CO, and then a mixture of 7.4 g (100 mmoles) of lime and 30 ml of $H_2O$ were added. After 850 psi CO was charged to the autoclave, the reaction mixture was heated to 80° C. over a period of time of approximately 1 hour and held at that temperature for 15 hours. The CO uptake stopped after 11 hours. After centrifugation, the solid was rinsed once with a 20 ml portion of a 50:50 t-butanol/water solution and then acidified with 150 ml of HCl solution containing ~100 mmoles of HCl. The free acid was extracted from the aqueous solution with diethyl ehter (2×120 ml) to give a 62% yield of cyclopropylglyoxylic acid based on proton NMR data with internal standard.

Having described the process which Applicants regard as their invention, it should be recognized that changes and variations within the scope and spirit of the invention can be made by one skilled in the art and it is accordingly to be understood that the present description of the invention is illustrative only. It is desired that the invention be limited only by the lawful scope of the following claims.

We claim:

1. A process for the production of cyclic-keto-acids of the general formula:

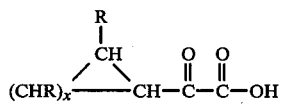

where R is hydrogen or a monovalent alkyl radical which can be either straight chain or branched having from 1 to about 20 carbon atoms and X=1, 3, or 4 which comprises reacting a functionalized 1-bromoalkane of the formula:

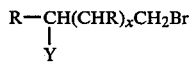

where R and X are as defined abovee and Y represents a leaving group selected from the group consisting of halogens, nitrates, sulfonates, and acetates, in a liquid solvent medium, with carbon monoxide at elevated temperature of 30° to 150° C. and elevated pressure of 300 to 3000 psig in the presence of a catalytic amount of a metal carbonyl compound and an alkali or an alkaline earth metal inorganic base.

2. A process according to claim 1, wherein the functionalized 1-bromoalkane is selected from 1-bromo-3-chloro- or 3-bromopropane, butane, pentane, hexane, heptane, octane, nonane, decane, undecane, dodecane, tridecane, tetradecane, pentadecane, hexadecane, heptadecane, octadecane, nonadecane, eicosane,; 1-bromo-5-chloro- or 5-bromopentane, hexane, heptane, octane, nonane, decane, undecane, dodecane, tridecane, tetradecane, pentadecane, hexadecane, heptadecane, octadecane, nonadecane, eicosane,; 1-bromo-6-chloro- or 6-bromohexane, heptane, octane, nonane, decane, undecane, dodecane, tridecane, tetradecane, pentadecane, hexadecane, heptadecane, octadecane, nonadecane, eicosane,.

3. A process according to claim 1, wherein the carbon monoxide pressure is from about 500 to 1000 psig.

4. A process according to claim 1, wherein the reaction is carried out at a temperature of from about 50° C. to about 100° C.

5. A process according to claim 1, wherein the inorganic base is selected from LiOH, NaOH, KOH, RbOH, Ca(OH)$_2$, Ba(OH)$_2$ or Mg(OH)$_2$.

6. A process according to claim 1, wherein the molar ratio of the inorganic base is from about 1 to 10 moles per mole of 1-bromoalkane reactant.

7. A process according to claim 1, wherein the metal carbonyl catalyst compound is iron pentacarbonyl, dicobalt-octacarbonyl of nickel-tetracarbonyl.

8. A process according to claim 7, wherein the metal carbonyl is dicobalt-octacarbonyl.

9. A process according to claim 7, wherein the metal carbonyl catalyst compound is a salt of iron pentacarbonyl, dicobalt-octacarbonyl or nickel-tetracarbonyl.

10. A process according to claim 9, wherein said salt is sodium, potassium or calcium.

11. A process according to claim 1, wherein the catalyst is formed by carbonylation in organic solvent and used in that solvent.

12. A process according to claim 1, wherein the molar percentage of the metal carbonyl compound to the functionalized 1-bromoalkane is from about 0.1 to about 25%.

13. A process according to claim 1, wherein the liquid solvent medium is a mixture of water and alcohol.

14. A process according to claim 13, wherein the mixture consists of from about 10% to about 90% by weight water and from about 90% to about 10% alcohol.

15. A process according to claim 13, wherein the alcohol is a saturated, linear or branched, aliphatic, monohydroxylic or polyhydroxylic compound containing up to 6 carbon atoms.

16. A process according to claim 15, wherein the alcohol is tert-butanol.

17. A process according to claim 15, wherein the alcohol is isopropanol.

18. A process according to claim 1 wherein Y is a halogen.

* * * * *